United States Patent [19]

Weigelt

[11] Patent Number: 4,878,602
[45] Date of Patent: Nov. 7, 1989

[54] FOOT-ACTUATED POWDER DISPENSER

[76] Inventor: Peter Weigelt, 5974 Buckingham Pky., #401, Culver City, Calif. 90230

[21] Appl. No.: 269,485

[22] Filed: Nov. 10, 1988

[51] Int. Cl.⁴ ............................................. A61M 35/00
[52] U.S. Cl. ................................... 222/161; 604/293;
222/179; 222/181; 222/196; 222/565
[58] Field of Search .............. 222/160, 161, 179, 181,
222/185, 196, 565; 604/58, 293

[56] References Cited

U.S. PATENT DOCUMENTS

| 2,484,659 | 10/1949 | Swerdlow et al. | 604/293 |
|---|---|---|---|
| 2,552,817 | 5/1951 | Ross | 222/108 |
| 2,801,773 | 8/1957 | Vitkin | 222/161 X |
| 2,906,578 | 9/1959 | Sessions | 222/108 X |
| 3,059,815 | 10/1962 | Parsons, Jr. | 222/108 X |
| 3,130,726 | 4/1964 | Rich | 604/293 |
| 3,378,009 | 4/1968 | Peplin | 604/293 |
| 3,643,838 | 2/1972 | Allen | 222/565 X |
| 3,683,896 | 8/1972 | Peplin | 604/58 X |
| 4,029,096 | 6/1977 | Fust | 604/293 |
| 4,077,546 | 3/1978 | Winkelried | 222/179 |
| 4,170,046 | 10/1979 | Mattison | 222/179 X |

FOREIGN PATENT DOCUMENTS 641444 1/1937 Fed. Rep. of Germany ...... 604/293

Primary Examiner—Kevin P. Shaver

[57] ABSTRACT

A foot-activated powder dispenser comprising a generally cylindrical dispenser member having a plurality of openings formed in the bottom surface thereof. A treadle member, and a device resiliently supporting the dispenser member above the treadle member. An actuator device coupling the treadle member to said dispenser member to permit movement of the dispenser member by the treadle member. A stop positioned in the path of movement of the dispenser member to abruptly halt movement of the dispenser member by the treadle member and to cause powder contained in the dispenser to the dislodged through the openings for application to the foot on the treadle member.

16 Claims, 2 Drawing Sheets

FOOT-ACTUATED POWDER DISPENSER

BACKGROUND

1. Field of Invention

This invention relates to powder dispensers and is particularly directed to foot-actuated powder dispensers for use by disadvantaged persons having little or no use of their hands.

2. Prior Art

The use of foot powder for preventing foot odor, perspiration, fungal infections and the like is common practice. Conventionally, the foot powder is packaged in a shaker-type dispenser which the user holds in their hand and shakes to apply the powder. However, for persons confined to wheelchairs, and those who have little or no use of their hands, the use of such shaker-type dispensers is extremely difficult, if not impossible. Numerous attempts to overcome this problem have been proposed heretofore. However, none of the prior devices have been entirely satisfactory. Many of the prior art devices have been complex and expensive to produce and maintain. Others have simply failed to properly address the limitations of disadvantaged persons. A search in the United States Patent Office has revealed the following references:

| U.S. PAT. NO. | INVENTOR | ISSUED |
| --- | --- | --- |
| 2,484,659 | M. H. Swerdlow | Oct. 11, 1949 |
| 3,130,726 | E. Rich | Apr. 28, 1964 |
| 3,344,958 | J. Kaanehe | Oct. 3, 1967 |
| 4,077,546 | I. Winkelried | Mar. 7, 1978 |
| 4,316,558 | R. J. Kubiak | Feb. 23, 1982 |
| 4,532,668 | A. Slonickis | Aug. 6, 1985 |

The patents to Rich and Swerdlow each disclose foot-actuated powder dispensers wherein the foot compresses a flexible airbag which serves to blow the powder onto the foot. However, such flexible airbags are subject to cracking which renders them useless. Also, powder stored in devices of this sort tends to become caked and, hence, cannot be blown onto the foot. The patent to Winkelried discloses a foot-actuation of an aerosol can. However, proper use of aerosol cans usually requires that the can be shaken prior to use, which is impossible with the Winkelried device. Furthermore, aerosol cans generally employ fluorocarbons as propellants. However, these chemicals have been found to be detrimental to the earth's atmosphere and their use is being discouraged. The remaining references relate to manually operated devices which, obviously, fail to address the problems overcome by the present invention.

BRIEF SUMMARY AND OBJECTS OF INVENTION

These disadvantages of prior art powder dispensers are overcome with the present invention and a foot-activated powder dispenser is provided which is simple and inexpensive to produce and maintain and which prevents caking of powder within the dispenser during intervals of non-use.

The advantages of the present invention are preferably attained by providing a foot-activated powder dispenser comprising a generally cylindrical dispenser member having a plurality of openings formed in the bottom surface thereof, a treadle member, means resiliently supporting said dispenser member above said treadle member, actuator means coupling said treadle member to said disenser member to permit movement of said dispenser member by said treadle member, and stop means positioned in the path of movement of said dispenser member to abruptly halt movement of said dispenser member by said treadle member and to cause powder contained in said dispenser to be dislodged through said openings for application to the foot on said treadle member.

Accordingly, it is an object of the present invention to provide improved foot powder dispensers.

Another object of the present invention is to provide improved foot-actuated powder dispensers.

A further object of the present invention is to provide improved foot powder dispensers for use by disadvantaged persons confined to wheelchairs or having little or no use of their hands.

A specific object of the present invention is to provide a foot-activated powder dispenser comprising a generally cylindrical dispenser member having a plurality of openings formed in the bottom surface thereof, a treadle member, means resiliently supporting said dispenser member above said treadle member, actuator means coupling said treadle member to said dispenser member to permit movement of said dispenser member by said treadle member, and stop means positioned in the path of movement of said dispenser member to abruptly halt movement of said dispenser member by said treadle member and to cause powder contained in said dispenser to be dislodged through said openings for application to the foot on said treadle member.

These and other objects and features of the present invention will be apparent from the following detailed description, wherein reference is made to the figures of the accompanying drawings.

DETAILED DESCRIPTION OF THE INVENTION

Figure 1:
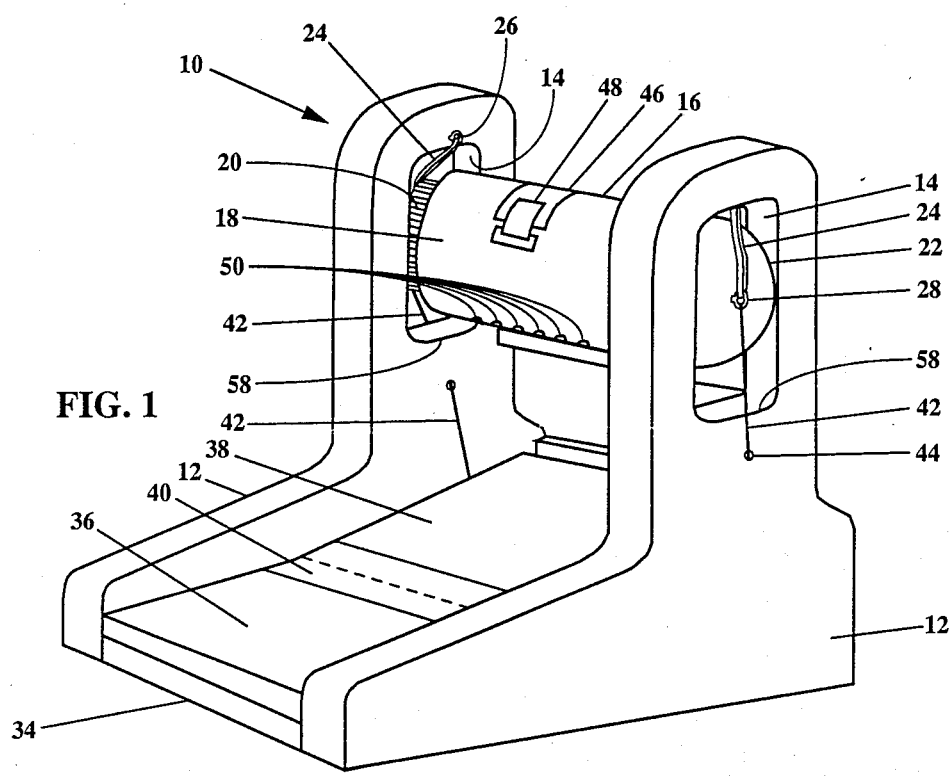
FIG. 1 is an isometric view of a foot powder dispenser embodying the present invention.
Figure 2:
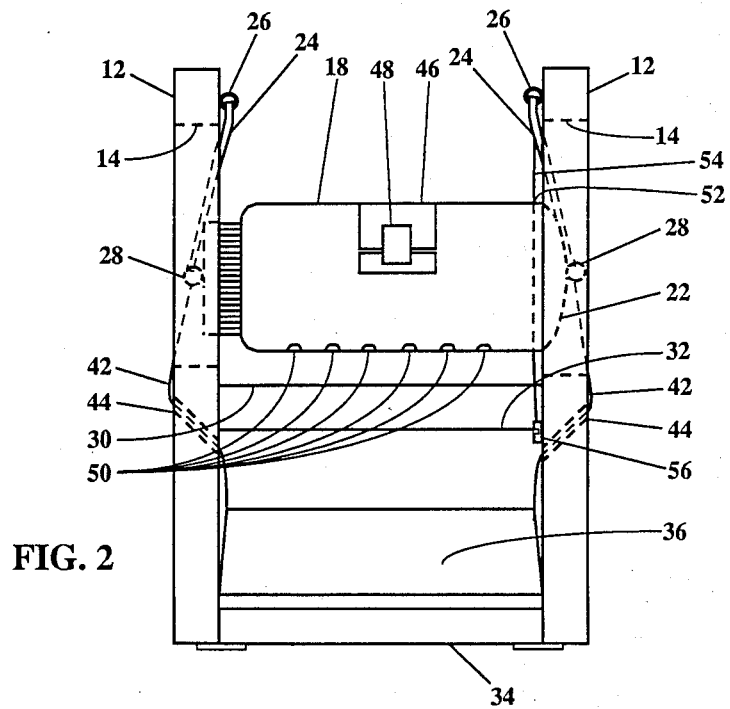
FIG. 2 is a front view of the foot powder dispenser of FIG. 1.
Figure 3:
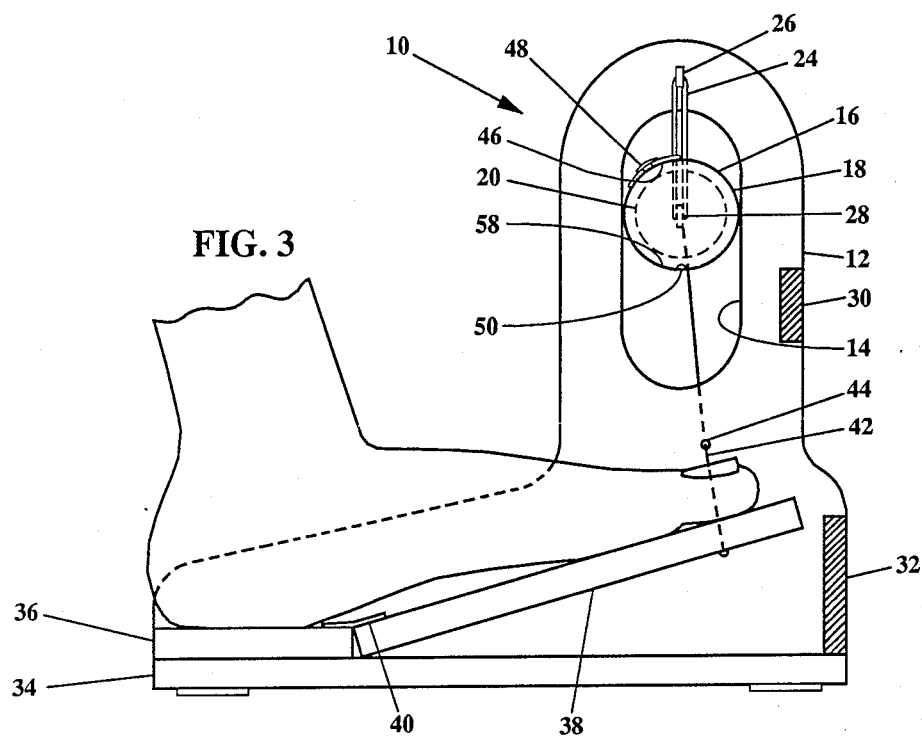
FIG. 3 is a side view, partly in section, through the foot powder dispenser of FIG. 1, showing the dispenser prior to actuation.
Figure 4:
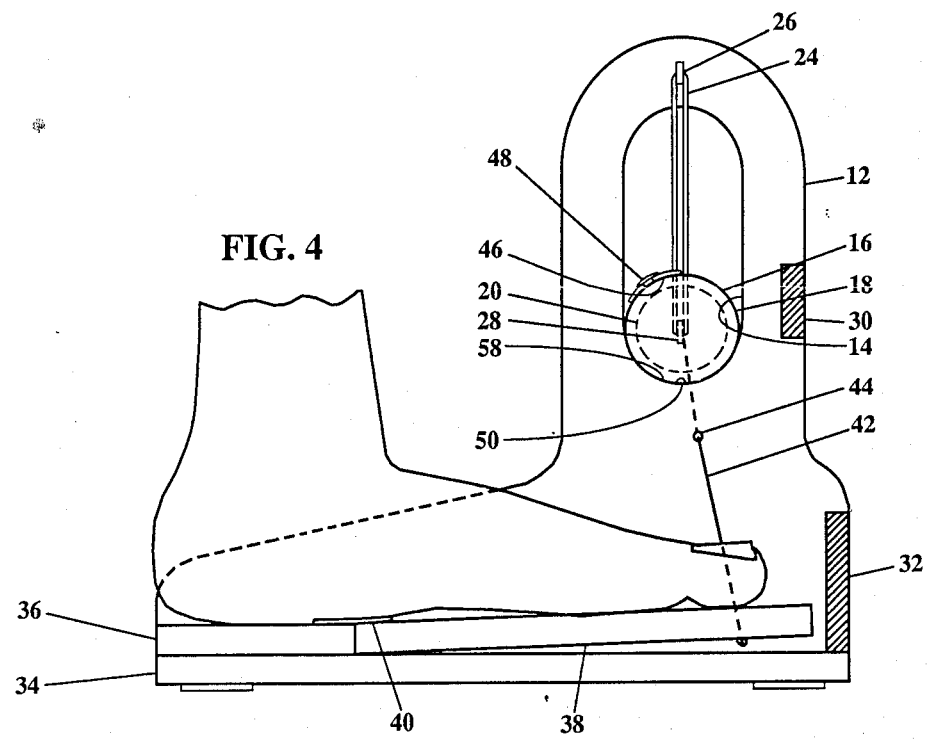
FIG. 4 is a view, similar to that of FIG. 3, showing the foot powder dispenser during actuation.

In that form of the present invention chosen for purposes of illustration in the drawings, FIG. 1 shows a foot powder dispenser, indicated generally at 10, comprising a pair of vertical supports 12 each formed with an elongated opening 14. A dispenser member 16 is provided having a generally cylindrical body portion 18 and a guide portion 20 of lesser diameter than the body portion 18 formed at one end of the body portion and projecting into the adjacent one of the openings 14 for slidable movement within the opening 14. The opposite end 22 of the dispenser member 16 is generally rounded and rides on the edges of the adjacent opening 14. The dispenser member 16 is supported by a pair of resilient means, such as elastic bands 24, and is normally maintained at a position approximately midway of the openings 14. The resilient means 24 are connected to the vertical supports 12 by suitable means, such as screws 26, and are connected to the dispenser member 16 by suitable attaching means, such as screw eyes 28. A pair of horizontal members 30 and 32 connect the rear of the support members 12 and also serve to prevent powder from falling out the rear of the dispenser 10. A horizontal base member 34 connects the support members 12 and a horizontal member 36 connects the support members 12 and also serves as a heel rest for the user's foot. A treadle member 38 is joined to the rear edge of horizontal member 36 by a hinge means 40 and extends rearwardly into proximity with the rear horizontal member 32. The treadle 38 is connected to the dispenser member 16 by actuating means, such as strings 42, having their upper ends connected to the attaching means 28 and having their lower ends connected to the treadle 38. As shown, the actuating means 42 pass downwardly outside the vertical support members 16 and pass inwardly through slanted holes 44 formed in the vertical support members 12 to attach to the underside of the treadle 38. A door 46 is provided in the dispensing member 16 to permit renewing the supply of powder inside the dispensing member 16 and suitable retaining means 48 serves to releasably secure the door 46 in its closed position. The retaining means 48 is shown as being a strip of hook and loop material, such as that available under the tradename "Velcro", available from Velcro U.S., Rochester, N.Y. The dispenser member 16 has a plurality of holes 50 provided on its lower side to permit powder to be dispensed therethrough from within the body portion 18. Finally, if desired, an opening 52 may be provided in the upper side of the body portion 18 of the dispenser member 16 and agitator means, such as string 54 may have one end secured to one of the attaching means 26 and may pass into opening 52 in the upper side of the body portion 18 of dispenser member 16 and out one of the openings 50 in the lower side of the body portion 18 of the dispenser member 16 to suitable lower attaching means, such as screw 56. The agitator means 54 serves to guide movement of the dispenser member 16 and, during such movement, serves to agitate the powder contained within the body portion 18 of the dispenser member 16 to prevent caking of the powder. In addition, the agitator means 54 serves to maintain the openings 50 oriented downwardly to assure proper dispensing of the powder.

In use, the body 18 of the dispenser member 16 is filled with a supply of powder through door 46 and the door is secured in its closed position by retaining means 48. Thereafter, resilient means 24 will normally maintain the dispenser member 16 suspended approximately midway of the openings 14 in the vertical support members 12. To dispense the powder, a user places his heel on the heel rest 36 and used the forward portion of his foot to depress the treadle 38. When the treadle 38 is depressed, actuating means 42 drives the dispenser member 16 downward causing the dispenser member 16 to strike sharply against the bottom 58 of the elongated openings 14 of the vertical support members 12, which causes powder to be dispensed through the holes 50 in the bottom side of the body portio 18 of the dispenser member 16. Upon release of pressure on the treadle 38, the resilient means 24 will return the dispenser member 16 to its normal position in readiness for subsequent actuation. As this occurs, agitator means 54 will serve to guide movement of the dispenser member 16 and, as the agitator means moves through the body portion 18 of the dispenser member 16, the agitator means 54 will agitate the powder within the body portion 18 and, hence, will serve to prevent caking of the powder and possible clogging of the holes 50. Also, the agitator 54 serves to prevent rotation of the dispenser member 16 to assure that the holes 50 are oriented downwardly.

It will be apparent to those skilled in the art that springs, pneumatic cylinders or other similar means could, if desired, be substituted for the elastic bands shown as resilient means 24. Moreover, strips of flexible material, such as leather or plastic, could be employed as the hinge means 40. Also, if desired, latching means, such as a hook and eye, could be substituted for the hook and loop strip as the retaining means 48 for door 46 of the dispenser means 16. In addition, numerous other variations and modifications may, obviously, be made without departing from the spirit of the present invention. Therefore, it should be clearly understood that the form of the present invention described above and shown in the figures of the accompanying drawings is illustrative only and is not intended to limit the scope of the present invention.

What is claimed is:

1. A foot-actuated powder dispenser comprising:
a pair of vertical support members each having an elongated opening formed therein,
a generally cylindrical dispenser member having a plurality of openings formed in the bottom surface thereof,
resilient means normally suspending said dispenser member from said support members approximately midway of said elongated openings,
a treadle member hingedly secured to the lower portions of said support members,
actuator means coupling said treadle member to move said dispenser member downwardly against the action of said resilient means, and
stop means positioned in the path of movement of said dispenser member to abruptly halt downward movement of said dispenser member and to cause powder contained in said dispenser to be dislodged through said openings for application to the foot on said treadle member.

2. The dispenser of claim 1 wherein:
said dispenser member has a reduced diameter portion slidable within said elongated openings.

3. The dispenser of claim 1 wherein:
said dispenser member has a door formed in the body portion thereof to permit supplying powder to the interior of said body portion for dispensing therefrom.

4. The dispenser of claim 1 wherein:
said resilient means in an elastic band.

5. The dispenser of claim 1 wherein:
said resilient means is a spring.

6. The dispenser of claim 1 wherein:
said treadle member is secured to said support members by a hinge formed of leather.

7. The dispenser of claim 1 wherein:
said treadle member is secured to said support members by a hinge formed of plastic material.

8. The dispenser of claim 1 wherein:
said stop means is the bottom of at least one of said elongated openings.

9. The dispenser of claim 1 wherein:
said actuator means is a string.

10. The dispenser of claim 1 further comprising:
agitator means operable within said body porition of said dispenser member to agitate powder contained within said body portion to prevent caking of said powder.

11. The dispenser of claim 10 wherein said agitator means comprises:
an opening formed in the upper surface of said body portion of said dispenser member, and
means passing through the upper opening and one of the plurality of bottom openings of said dispenser member to cause agitation of powder in said dispenser during movement of said dispenser.

12. The dispenser of claim 11 wherein:
said last named means is a string.

13. The dispenser of claim 1 further comprising:
a hole formed in the upper and surface of said dispenser member, and
alignment means extending through said hole and one of the plurality of bottom openings to prevent rotation of said dispenser member.

14. The dispenser of claim 13 wherein:
said alignment means is a string.

15. The dispenser of claim 1 further comprising:
agitator means extending through said dispenser member to agitate the powder in said dispenser member to prevent caking of said powder.

16. The dispenser of claim 15 wherein:
said agitator means is a string extending through said dispenser member.

* * * * *